US008825132B2

(12) United States Patent
Lohman et al.

(10) Patent No.: US 8,825,132 B2
(45) Date of Patent: Sep. 2, 2014

(54) FIELD CYCLING METHOD FOR MAGNETIC RESONANCE

(75) Inventors: Joost Lohman, Kenilworth (GB); Simon Benedict Duckett, York (GB); Gary George Green, Benton (GB); Antonio Giuseppe Gianotti, Heidelberg (DE)

(73) Assignees: Bruker BioSpin GmbH, Rheinstetten (DE); The University of York, Heslington, York (GB)

( * ) Notice: Subject to any disclaimer, the term of this patent is extended or adjusted under 35 U.S.C. 154(b) by 18 days.

(21) Appl. No.: 13/541,688

(22) Filed: Jul. 4, 2012

(65) Prior Publication Data

US 2014/0012129 A1 Jan. 9, 2014

(51) Int. Cl.
*A61B 5/055* (2006.01)
*G01V 3/00* (2006.01)

(52) U.S. Cl.
USPC .......................................... 600/420; 324/309

(58) Field of Classification Search
USPC .................. 600/410, 419, 420; 324/307, 309
See application file for complete search history.

(56) References Cited

U.S. PATENT DOCUMENTS

| 5,144,238 | A | 9/1992 | Ehnholm |
| 6,466,814 | B1 | 10/2002 | Ardenkjaer-Larsen et al. |
| 7,474,095 | B2 | 1/2009 | Levitt |
| 7,750,633 | B2 | 7/2010 | Pines |
| 2010/0219826 | A1* | 9/2010 | Duckett et al. ............... 324/307 |
| 2012/0176130 | A1* | 7/2012 | Ledbetter et al. ............ 324/301 |

FOREIGN PATENT DOCUMENTS

| WO | WO 2008/155093 | 12/2008 |
| WO | WO 2010/048708 | 5/2010 |

OTHER PUBLICATIONS

Jan H. Ardenkjaer-Larsen et al., "Increase in signal-to-noise ratio of >10,000 times in liquid-state NMR", 10158-10163, PNAS, Sep. 2, 2003, vol. 100, No. 18.
Johannes Natterer et al., "Parahydrogen induced polarization", Progress in Nuclear Magnetic Resonance Spectroscopy 31 (1997) 293-315.
Ralph W. Adams et al., "Reversible Interactions with para-Hydrogen Enhance NMR Sensitivity by Polarization Transfer", Mar. 27, 2009, vol. 323, Science, 1708-1711.
Maria Belén Franzoni et al., "Long-Lived $^1$H Singlet Spin states Originating from Para-Hydrogen in Cs-Symmetric Molecules Stored for Minutes in High Magnetic Fields", J. Am. Chem. Soc., 2012, 134 (25), pp. 10393-10396.
Green, Richard A. et al., "The theory and practice of hyperpolarization in magnetic resonance using parahydrogen", Progress in Nuclear Magnetic Resonance Spectroscopy 67 (2012) 1-48.

* cited by examiner

*Primary Examiner* — Michael Rozanski
(74) *Attorney, Agent, or Firm* — Paul Vincent

(57) ABSTRACT

An NMR experiment on hyperpolarizable magnetic nuclei of substrate molecules in a living human or animal body, involves polarizing the substrate molecules by non-hydrogenating para-hydrogen induced polarization (=NH-PHIP) into a singlet/pseudo singlet state in low magnetic field and injecting the substrate molecules into the living body, the body or a part thereof being previously located inside a magnet at low magnetic field. The magnet is switched on to high magnetic field, and in at least part of the substrate molecules, the singlet state/pseudo singlet state is converted into observable magnetization. An MRI or MRS measurement is carried out with the living body or the part thereof, collecting data from the substrate molecules. The NMR experiment is well applicable on hyperpolarized nuclei within a patient, with reduced losses of magnetization due to relaxation processes.

26 Claims, 3 Drawing Sheets

FIELD CYCLING METHOD FOR MAGNETIC RESONANCE

BACKGROUND OF THE INVENTION

The invention relates to a method for carrying out an MRI (magnetic resonance imaging) or MRS (magnetic resonance spectroscopy) experiment on hyperpolarizable magnetic nuclei of substrate molecules and/or their metabolites contained in a living human or animal body.

NMR (nuclear magnetic resonance) techniques may be applied to gather information about a sample or sample area in a gentle, non-destructive way; in particular, clinical investigations on living patients can be done non-invasively.

However, NMR techniques are generally limited by a low sensitivity, i.e. low signal intensities. In order to improve the sensitivity, NMR experiments are performed in a static magnetic fields of high field strength such as of 1.5 T and above. Such fields are generated by superconducting magnets.

Further, the sensitivity may be increased by applying hyperpolarization techniques. Here, nuclei in a sample are prepared with a polarization level higher than corresponding to the Boltzmann distribution at the sample's temperature and the prevailing magnetic field strength, and the hyperpolarized nuclei undergo the NMR experiment. A common hyperpolarization technique is dissolution dynamic nuclear polarization (dissolution DNP), see e.g. U.S. Pat. No. 6,466,814 B1. A particularly promising hyperpolarization technique is NH-PHIP (non-hydrogenating para-hydrogen induced polarization), compare WO 2008/155093 A1.

The preparation of a hyperpolarized sample typically occurs outside the magnet used for an NMR experiment. Accordingly, the hyperpolarized sample has to be transported to said magnet, and this delay will lead to a loss of magnetization through relaxation.

Relaxation is a particularly severe problem in in vivo NMR experiments, in particular in NMR imaging. Here, time is needed to allow the hyperpolarized nuclei to migrate to the area of interest, e.g. via the blood stream, and possibly to allow a metabolic process to evolve.

In U.S. Pat. No. 7,474,095 B2 it has been proposed to prepare a sample with molecules polarized in a long-lived singlet or pseudo singlet state, and to convert this state into observable magnetization before an NMR measurement. Franzoni et al. [4] showed that long lived 1H singlet spin states originating from parahydrogen could be stored for minutes in a high magnetic field of about 7 T, and converted into triplet states by level anticrossing, involving changing the sample position to a low field area of about 0.1 T.

It is the object of the invention to provide a method for carrying out an MRI or MRS experiment which is well applicable to hyperpolarized nuclei within a living human or animal body, with reduced losses of magnetization due to relaxation processes.

SUMMARY OF THE INVENTION

This object is achieved, in accordance with the invention, by a method for carrying out an MRI or MRS experiment on hyperpolarizable magnetic nuclei of substrate molecules and/or their metabolites contained in a living human or animal body, with the following steps:
a) the substrate molecules are polarized by non-hydrogenating para-hydrogen induced polarization (=NH-PHIP) into a singlet state or pseudo singlet state in an environment of a static magnetic field lower than 100 mT, in particular lower than 10 mT;
b) the substrate molecules in the singlet state or pseudo singlet state are injected into the living human or animal body, wherein said human or animal body or a part thereof is already located inside a magnet with a static magnetic field lower than 100 mT, in particular lower than 10 mT;
c) the magnet is switched on to a static magnetic field strength inside the magnet higher than 200 mT, in particular higher than 500 mT, and in at least a part of the substrate molecules and/or their metabolites in the singlet state or pseudo singlet state, the singlet state or the pseudo singlet state is converted into observable magnetisation;
d) an MRI or MRS measurement is carried out with the living human or animal body or the part thereof contained inside the magnet, collecting data from the substrate molecules and/or their metabolites.

The invention proposes to generate hyperpolarized substrate molecules by means of NH-PHIP. NH-PHIP is described in detail in WO 2008/155093 A1, the content of which is herewith incorporated by reference. NH-PHIP is a particularly suited method for creating hyperpolarized molecules in long-lived singlet or pseudo singlet states, especially when applied at a (very) low magnetic field.

When performing the NH-PHIP in a low static magnetic field, as stated in step a), long-lived singlet or pseudo singlet states can easily be generated in the substrate molecules.

Subsequently, in step b), the hyperpolarized substrate molecules in the singlet or pseudo singlet state are injected into the living human or animal body (patient). Said patient or a body part of interest thereof is already positioned inside a magnet which is to be used for the intended NMR experiment. At this time, the magnet is in a low field state (typically it is completely switched-off/currentless); this keeps the substrate molecules in the singlet or pseudo singlet state. Accordingly, time for migration of the substrate molecules or metabolic processes within the patient is available still with the substrate molecules in the long-lived spin state, and relaxation losses are not yet relevant.

Then, in step c), the magnet is switched on, and the unobservable singlet or pseudo singlet state of the substrate molecules is converted into observable magnetization. Often and preferably, the increase in the magnetic field strength alone effects the conversion.

Immediately afterwards, an NMR measurement may begin in step d), so magnetization losses due to relaxation are kept to a minimum, in accordance with the invention. Typically, the static magnetic field is maintained high during step d), e.g. at the field strength reached in step c) before.

Typically, during steps a) and b), there is no artificially generated static magnetic field at all, but only the earth's magnetic field (so the magnet is switched off). Note that in accordance with the invention, in step a) and/or step b) there may be even no static magnetic field at all.

In NH-PHIP the magnetisation of parahydrogen, which exists in a pure singlet state, is transferred to magnetic nuclei in the hyperpolarizable substrate molecules, thereby creating a plurality of magnetic states. Some of these states may be invariant under pair wise exchange of nuclei in the molecule because of the molecular symmetry. We will refer to these states as singlet states. Even in non-symmetric molecules some magnetic states may be invariant under pair wise exchange of nuclei if they are magnetically equivalent or nearly equivalent such as for instance at low magnetic field where the Zeeman interaction energy is smaller than the spin-spin interaction energy. We will refer to these states as pseudo singlet states.

Singlet or pseudo singlet states have in general a substantially longer life time than magnetic states that decay with the longitudinal relaxation time $T_1$. The singlet or pseudo singlet states of the substrate molecules or their magnetic nuclei typically have a lifetime of at least two times, preferably at least five times, most preferably at least ten times longer than the average longitudinal relaxation time T1 of hyperpolarized nuclei of the substrate molecule in non-singlet and non-pseudo singlet states; the lifetime of a singlet or pseudo singlet state is often longer than 30 seconds.

In the most simple case, in step a) protons are polarized in the substrate molecules, and in step d) protons are measured in the NMR measurement. Alternatively, in step a) protons are polarized in the substrate molecules, and after a polarization transfer, in step d) a non-hydrogen nucleus such as $^{13}C$ or $^{15}N$ is measured. Further alternatively, in step a), a non-hydrogen nucleus such as $^{13}C$ or $^{15}N$ (which is present in the substrate molecules at least twice, typically due to labelling) is polarized, and in step d), this non-hydrogen nucleus is measured.

Note that the invention may be generalized beyond the living human or animal body: Then the MRI or MRS experiment is carried out on hyperpolarizable nuclei of substrate molecules and/or their derivatives contained in a subject of interest (which may be a living human or animal body, but also a non-biological and non-living subject, such as a reaction vessel or sample carrier). In step b), the substrate molecules are transferred into the subject of interest, wherein the subject of interest or a part thereof is already located inside the magnet. In step c), in at least a part of the substrate molecules and/or their derivatives in the singlet state or pseudo singlet state, the singlet state or the pseudo singlet state is converted into observable magnetization, and in step d), the MRI or MRS measurement is carried out on the subject of interest or the part thereof, collecting data from the substrate molecules and/or its derivatives.

Rapid Field Switching

In a preferred variant of the inventive method, the magnet is switched on over a time of 5 s or less, preferably 1 s or less, most preferably 0.5 s or less. Then relaxation losses during the build-up of the static magnetic field are kept low.

Particularly preferred is a variant wherein the magnet used in the method is of non-superconducting type. In a non-superconducting (electro-)magnet, a switching of the current is particularly simple. The magnet typically comprises one or several magnet coils, such as of solenoid type, wherein the human or animal body or the part thereof is typically located in a bore of the magnet coil(s).

Variants Relating to the Conversion

In an advantageous variant, in step c), the singlet state or pseudo singlet state of at least part of the substrate molecules and/or their metabolites is converted into observable magnetization spontaneously. In other words, apart from the switching of the static magnetic field, no further measures contribute to the magnetization conversion for said at least part. This is particularly simple; no additional equipment is needed. Preferably, there is only spontaneous conversion of the singlet state or pseudo singlet state of the substrate molecules (and/or their metabolites). If a significant fraction of the substrate molecules (and/or their metabolites) in the singlet or pseudo singlet state does not convert spontaneously, additional measures to facilitate the conversion may be undertaken (see below).

A preferred variant provides that during steps a) through b) a spin-locking oscillating magnetic field is applied, preventing a conversion of the singlet or pseudo singlet state into observable magnetization, and that in step c), the spin-locking oscillating magnetic field is switched off. The spin-locking field (typically an RF field; with RF: radio frequency) may stabilize the singlet or pseudo singlet state of the substrate molecules and/or their metabolites during steps a) and b); after it is switched off, conversion is enhanced and/or effected.

In another preferred variant, in step c), an RF pulse sequence and/or a gradient pulse sequence is applied. The RF or gradient pulse sequence may be applied to enhance and/or effect the conversion of the singlet state or pseudo singlet state into observable magnetization. It is also possible to apply an RF pulse sequence to convert an unobservable intermediate spin state of the substrate molecules (such as a multiple quantum state), which has been assumed typically spontaneously in the course of step c), into observable magnetization.

Also preferred is a variant wherein in step c), the substrate molecule and/or its metabolite is chemically reacted or brought into contact with a conversion molecule. The conversion molecule may be used to enhance and/or effect the conversion of the singlet state or pseudo singlet state into observable magnetization. The conversion molecule is typically injected as a solution into the human or animal body after step b). In the general case, the substrate molecule and/or its derivatives are chemically reacted or brought into contact with the conversion molecule; the conversion molecule is typically transferred into the subject of interest as a solution after step b).

In an advantageous variant of the inventive method, the method comprises the following further steps:

e) the magnet is switched to a static magnetic field strength inside the magnet lower than 100 mT, in particular lower than 10 mT, and/or a spin-locking oscillating magnetic field is applied;

f) the magnet is switched on to a static magnetic field strength inside the magnet higher than 200 mT, in particular higher than 500 mT, and/or the spin-locking oscillating magnetic field is switched off, and in at least part of the remaining substrate molecules and/or their metabolites in the singlet state or pseudo singlet state, the singlet state or pseudo singlet state is converted into observable magnetisation;

g) a further MRI or MRS measurement is carried out with the living human or animal body or the part thereof contained inside the magnet, collecting data from the substrate molecules and/or their metabolites;

wherein the steps e) through g) are repeated at least once. This variant extends the time window for the NMR experiment or its NMR measurements, respectively. During steps e) and f), a new measurement step may be prepared; the number of repetitions can be adapted to the needs of the NMR experiment. Steps e) through g) are performed at least once; however, typically, steps e) through g) are performed two, three or four times. In the course of step e), the remaining observable magnetisation may be reconverted into singlet state or pseudo singlet state; at least no further conversion from (pseudo) singlet state to observable magnetisation takes place here. However it is also possible that preceding step c) and/or possibly one or several steps f) were done with converting only part of the substrate molecules (and/or their metabolites) in the singlet or pseudo singlet state into observable magnetization. In the general case, step f) is applied to the substrate molecules and/or their derivatives, and in step g) the further MRI or MRS measurement is carried out on the subject of interest or the part thereof, collecting data from the substrate molecules and/or its derivatives.

In an advantageous further development of the above variant, in step c) and optionally one or several steps f) the substrate molecule is chemically reacted or brought into contact with a conversion molecule, with the amount of the conversion molecule chosen small enough that only a part, in particular 50% or less, of the substrate molecules and/or their metabolites in the singlet state or pseudo singlet state are affected by the conversion into observable magnetization. The conversion molecules can be injected into the patient in several doses of a small bolus each, with each dose opening a new time frame for an NMR measurement, with a further part of the polarized substrate molecules and/or their metabolites. This is particularly simple with a conversion molecule chemically reacting with the substrate molecule or its metabolite.

In another advantageous further development, in step d) and optionally one or several steps g) only part of the observable magnetization is measured, in particular by applying a small flip angle excitation pulse, preferably with a flip angle of 45° or smaller. Here only part of the polarization of (all) substrate molecules and/or their metabolites is used (or used up) during each NMR measurement in steps d) and g); no dedicated conversion molecules are necessary here.

Advantageous is a variant wherein during or after step c), a polarization transfer from 1H to other nuclei, in particular 13C or 15N or 19F or 31P, in the substrate molecules is effected by means of an RF and/or gradient pulse sequence. In other words, a cross polarization step is applied before step d). This variant is typically applied when hyperpolarization of 1H can be achieved more easily than hyperpolarization of the other nuclei by NH-PHIP.

Static Magnetic Field

In a particularly preferred variant, step a) is performed in an environment with a static magnetic field lower than 1 mT, preferably lower than 100 µT. This particularly simple, and keeps the Zeemann energy low. Typically, step a) is done in the earth's magnetic field between 30 µT and 60 µT.

Also preferred is a variant wherein step a) is performed in an environment shielded from the earth's magnetic field, such that the static magnetic field strength in the shielded environment is below 10 µT. This variant allows an even lower Zeemann energy. If step a) is performed inside the magnet, the shielded environment can e.g. be created by applying current through suitably adapted gradient coils during step a) such as to counteract the earth's magnetic field; gradient coils may be used for generating a compensating field by reversing the current in one half of their windings.

In another preferred variant, in step b) the static magnetic field inside the magnet is lower than 1 mT, preferably lower than 100 µT. This is particularly simple again, and keeps the Zeemann energy low. Typically, step b) is performed in the earth's magnetic field between 30 µT and 60 µT.

Also preferred is a variant wherein the magnet is shielded from the earth's magnetic field, such that in step b) the static magnetic field inside the magnet is below 10 µT. This variant allows an even lower Zeemann energy again. The shielded environment can e.g. be created by applying current through the suitably adapted gradient coils during step b) such as to counteract the earth's magnetic field.

In a particularly preferred variant, the static magnetic field in step a) is chosen small enough such that the Zeeman energy of the hyperpolarizable magnetic nuclei in the substrate molecules is lower than or equal to their spin-spin interaction energy. This variant is particularly suitable for a substrate molecule with a low degree of symmetry. Then, at very low fields (typically 1 mT or less), the formation of singlet states in the substrate molecule is predominant in step a). Typically, the static magnetic field inside the magnet in step b) is chosen with the same conditions as in step a).

Further preferred is a variant providing that in step a), the static magnetic field is chosen such that the Zeeman energy of the hyperpolarizable magnetic nuclei in the substrate molecule is larger than their spin-spin interaction energy, and the polarization process is carried out for a prolonged period of time, not less than three times the average time required to transfer the polarisation of parahydrogen to the hyperpolarizable magnetic nuclei of the substrate molecules, preferably not less than five times said average time, most preferably not less than ten times said average time. At these energy correlations, a single catalytic interaction between parahydrogen and the substrate molecule typically results in a modest yield of singlet or pseudo singlet magnetization, and then, this variant allows an accumulation of the singlet state or pseudo singlet state in an iterative process through repeated catalytic interaction of parahydrogen and the (partially hyperpolarized) substrate molecule.

General Aspects

In an advantageous variant of the inventive method, step a) is done in a polarization device placed inside the magnet, in particular with a distance of 2 feet (0.6096 m) or less, preferably 1 foot (0.3048 m) or less, to the living human or animal body. By placing the polarization device inside the magnet, short distances and thus a quick and well-controlled transport of the substrate molecules may be assured. In the general case, the polarization device is placed within 2 feet (0.6096 m) or less, preferably within 1 foot (0.3048 m) or less, from the subject of interest. The magnet typically has a bore, and the polarization device may be placed within the bore then, together with the living human or animal body or the part thereof/together with the subject of interest or part thereof. When step a) is performed inside the magnet, suitably adapted gradient coils installed at the magnet can be used for shielding purposes; these are also available for step b).

In another advantageous variant, in step a), the substrate molecules are contained in a solution. For example, the solution is bubbled or diffused through with para-hydrogen, and a catalyst (enhancing the spin transfer from pH2 to the substrate molecules) is dissolved in the solution or is in contact with the solution (e.g. if the catalyst is solid). When the substrate molecules are in solution, the NH-PHIP process can be done easily. Moreover, further transport of the substrate molecules is simple.

A preferred further development of this variant provides that after step a), the solution containing the substrate molecules polarized in the singlet or pseudo-singlet state is converted into a biocompatible solution. The biocompatible solution may be safely injected into the living human or animal body, without harming it. If needed, the biocompatible solution is cooled or heated to a temperature acceptable for injection (typically between 10° C. and 40° C.).

Preferably, after step a), a catalyst is removed from the solution. The catalyst may be filtered out, if needed after precipitating it with a suitable agent. Catalysts for NH-PHIP may contain toxic heavy metals, which should be removed before injection.

Equally preferred is that after step a), the solution is degassed. This avoids introduction of gas into the patient's blood stream, so embolisms may be prevented.

In a preferred variant in step d), NMR signals altered by interaction with further molecules contained in the living human or animal body are collected from the substrate molecules and/or their metabolites. This is particularly useful for examination of metabolic processes. The interaction could just be limited to an approaching of the further molecules to the substrate molecules, without a chemical reaction; however, the inventive method may also be used to investigate chemical reactions of the substrate molecule. It is also possible, though, that the sample molecules simply spread in the human or animal body, and their distribution is studied. In the general case, NMR signals altered by interaction with further molecules contained in the subject of interest are collected from the substrate molecules and/or their derivatives.

Highly preferred is a variant wherein after step b), some time is allowed to pass for
- the substrate molecules to be transported to a region or organ of interest within the living human or animal body, in particular via the blood stream of the living human or animal body,
- and/or a metabolic process involving the substrate molecule to evolve. After step b) and before step c), when the substrate molecules are still in the singlet or pseudo-singlet state, the time allowed to pass hardly involves relaxation. A typical time waited after step b) is on the order of 1 s through 10 min; in many experiments a waiting time between 10 s and 60 s is useful. In the general case, after step b), some time is waited to allow the substrate molecules to be transported to a region of interest within the subject of interest, and/or a reaction process involving the substrate molecule to evolve (the latter typically resulting in a metabolite of the substrate molecule).

Also preferred is a variant the MRI or MRS experiment includes position sensitive NMR spectroscopy. The inventive method is particularly suited for this purpose.

Further within the scope of the present invention is the use of an above described inventive method for diagnosis and/or therapy monitoring. By means of the invention, high quality data about the living human or animal patient may be obtained.

Further advantages can be extracted from the description and the enclosed drawing. The features mentioned above and below can be used in accordance with the invention either individually or collectively in any combination. The embodiments mentioned are not to be understood as exhaustive enumeration but rather have exemplary character for the description of the invention.

The invention is shown in the drawing.

DESCRIPTION OF THE PREFERRED EMBODIMENT

Overview Over the Invention

Figure 1:
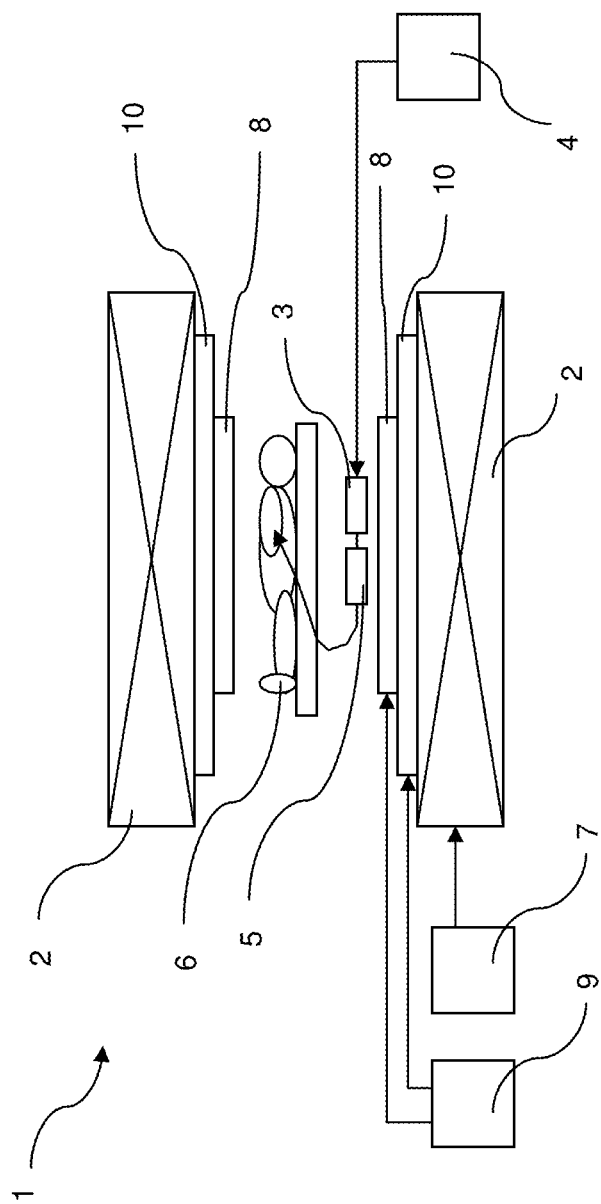
FIG. 1 shows schematically an experimental setup for performing the inventive method.

The invention relates to a field cycling method and an apparatus for magnetic resonance.

Hyperpolarisation is a well accepted method to enhance the sensitivity of NMR and MRI experiments and a number of methods have been described for the generation of hyperpolarised material (containing hyperpolarized substrate molecules). Two common methods are Dynamic Nuclear Polarisation (DNP) [1] and Para-Hydrogen Induced Hyperpolarisation (PHIP) [2]. These methods have in common that the hyperpolarised material is produced outside the magnet used for MR detection. As a consequence, the hyperpolarised material needs to be transferred to the MR magnet and, unavoidably, magnetisation will be lost through relaxation. This problem is particularly relevant in in vivo metabolic imaging where the hyperpolarised material is typically injected into the subject in the imaging magnet and extra time is required to allow the substrate molecules to be transported via the bloodstream to the area/organ of interest and, potentially, engage in a metabolic process.

One potential mitigation of this problem is to generate the hyperpolarised magnetisation in a singlet or pseudo singlet state which has a very much longer life time than normal magnetisation. Singlet states do not give rise to observable magnetisation but can be converted to such so they can be measured. There are various ways of producing (pseudo) singlet states and to convert them into observable magnetisation and examples are given in U.S. Pat. No. 7,474,095 B2 (Levitt et al.).

As disclosed in WO 2008/155093 A1, the polarisation of para-hydrogen ($pH_2$) can be transferred to a substrate molecule via a catalytic interaction which does not involve a hydrogenation step. This method was published under the acronym SABRE [3] and is referred to here as Non-Hydrogenating PHIP (NH-PHIP).

The polarisation transfer with NH-PHIP takes place at low magnetic field, lower than 1 T, preferably lower than 100 mT, or lower than 10 mT, or even lower, down to zero. $pH_2$ is in the magnetic singlet state and during transfer a mixture of magnetic states is created in the substrate molecule, depending on the magnetic field at which the transfer takes place. At zero field or, if the substrate molecule has a high degree of symmetry, at very low field, i.e. when the spin-spin interaction energy between the magnetic nuclei in the molecule is equivalent to or larger than their Zeeman energy, the formation of singlet states is predominant. This will typically occur when the magnetic field is lower than 1 mT or lower than 100 µT, or even lower than 10 µT. This method of generating singlet states is different from any of those described in U.S. Pat. No. 7,474,095 B2.

If the magnetic field is low, but the Zeeman energy of the nuclei in the molecule is still larger than their spin-spin interaction energy, then apart from singlet states, other magnetic states are polarised by the interaction with $pH_2$. These states will typically decay much more rapidly than the singlet states due to spin-lattice relaxation. Because of the reversible nature of the NH-PHIP process the fraction of the hyperpolarised magnetisation that has relaxed through this process will again be hyperpolarised, in the same ratio of singlet to non-singlet states. Through iteration of this process, simply by conducting the polarisation process for a sufficiently long period of time, a very large degree of singlet hyperpolarisation can be created. This mechanism is effective in a magnetic field e.g. of the order of the earth's magnetic field (30-60 µT).

There are several ways of converting (pseudo) singlet states into observable magnetisation:

1. If the substrate does not possess absolute symmetry but merely magnetic equivalence of the relevant nuclei at low field, then the magnetisation is not in a pure singlet state. In that case, transporting the substrate to higher field, or, alternatively, rapidly increasing the field at the position of the substrate, will remove the equivalence and the magnetisation becomes observable (and will no longer be long lived). It should be noted that this process starts during the change of field strength from low to high field.
2. If even at low field the magnetic equivalence alone is not sufficient to generate a long lived state, then it may be created in the presence of an RF spin-locking field to the relevant nuclei. Switching off the spin-locking field will render the magnetisation observable. If there is imperfect symmetry but the magnetic equivalence is high even at a relatively high magnetic field, or the magnetic equivalence is independent of field, as is for instance the case of symmetry in the chemical structure in combination with an asymmetric J-coupling network, then the singlet or long lived state can be converted into observable magnetisation by means of appropriate RF pulse sequences.

3. If the origin of the (pseudo) singlet state lies in the symmetry of the substrate molecule to the extent that it persists even at a relatively high field, then breaking of the symmetry by e.g. a chemical change will make the magnetisation observable.

According to this invention, the method to convert (pseudo) singlet states to observable magnetisation is by cycling the magnetic field, wherein the magnetic field strength at the position of the substrate molecule is increased to make the magnetization observable, in accordance with method number 1 noted above. However, the other methods 2 or 3 noted above may also (additionally) be employed in a field cycling apparatus in accordance with this invention.

The detection of MR signals is typically performed at high field for two main reasons:

The high signal strength resulting from the large thermal polarisation at high field.

The large chemical shift spectral dispersion.

In the case of the detection of hyperpolarised signals, the first argument is void. The second argument does not in general require the largest possible field, especially when detecting nuclei with a large intrinsic chemical shift dispersion such as e.g. $^{13}$C. It is therefore feasible to measure hyperpolarised MRI data at a much lower field than normally employed, even if chemical shift differentiation is required. Whereas traditional MRI magnets are of superconductive design and, consequently, cannot be switched rapidly, it is possible to design fast switching lower field magnets.

Fast switching magnets have been used in some MRI experiments. In general, a high field value is chosen to obtain sufficient thermal polarisation, following which the MRI experiment is conducted at low or zero field (U.S. Pat. No. 7,750,633 B2, Pines et al.). Sometimes, especially in relaxometry, detection takes again place at the high field (WO 2010 048708 A1, Alford et al.). In ESREMRI (aka OMRI or PEDRI), the sample injected into the subject contains free radicals. In this application, the subject is subjected to microwave irradiation at a low field, with the objective to enhance the nuclear polarisation by DNP, after which MR detection takes place at high field (U.S. Pat. No. 5,144,238 A, Ehnholm).

According to this invention, a method is described to perform hyperpolarised MRI whereby the loss in polarisation through relaxation is substantially reduced.

The inventive method typically comprises the following steps:

The NMR subject (patient or part thereof) is placed in a low field NMR magnet while the field is switched off. The subject therefore experiences the earth's magnetic field.

A solution containing the substrate molecule and a suitable catalyst is placed in a polarisation device in the earth's magnetic field. The polarisation device can be placed in close proximity to the subject.

The substrate molecule is polarised by NH-PHIP into a (pseudo) singlet state as described above. Optionally, an RF spin-locking field is employed during the polarisation process to maintain the singlet state.

While in the (pseudo) singlet state, the solution with the hyperpolarised substrate molecule is removed from the polarisation device and optionally treated to obtain a biocompatible injectable solution of the hyperpolarised substrate molecules in the (pseudo) singlet state.

The biocompatible solution is injected into the subject and time is allowed for the substrate molecules to be transported to the region/organ of interest and/or a metabolic process involving the substrate molecule to evolve as desired.

The magnet is rapidly switched on to the required field strength for an intended NMR experiment; typically, the (pseudo) singlet state is converted to observable magnetization by the field switching alone.

Optionally the (pseudo) singlet state is maintained by means of appropriate spin-locking RF fields.

Optionally, at the desired time, the (pseudo) singlet state is converted to observable magnetisation e.g. by means of methods 2, 3, or 4 in the list above.

The NMR (MRI or MRS) experiment is conducted collecting data from the substrate molecule and, optionally, from its metabolites.

The invention provides a novel manner in which (pseudo) singlet states are generated and uses a switching between low and high magnetic fields for NH-PHIP hyperpolarisation and MR detection respectively. The benefits lie in the much higher degree of control of the relaxation of the hyperpolarised material prior to the MR measurement, afforded by having a rapidly switchable magnet.

Description of a Field Cycling Apparatus for Use with an Inventive Method

FIG. 1 illustrates schematically an experimental setup, and more specifically a field cycling apparatus 1, for carrying out an NMR experiment according to the inventive method.

The field cycling apparatus 1 comprises a field cycling magnet 2 (also referred to simply as magnet) of normally-conducting type, in which is placed a polarisation device 3 for the hyperpolarisation of substrate molecules (typically in solution, preferably in an aqueous solution) within the polarisation device 3 by means of Non-Hydrogenative Para-Hydrogen Induced Polarisation (NH-PHIP).

The polarisation device 3 is supplied with parahydrogen gas by a parahydrogen supply device 4. Hyperpolarised substrate molecules are formed in the singlet or pseudo singlet state and injected or infused by means of injection/infusion device 5 into a living human or animal body (patient) 6. The injection/infusion device 5 contains provisions (see FIG. 2) for preparing a biocompatible solution of the hyperpolarised substrate molecules such as removing the catalyst used in the hyperpolarisation process or removing excess parahydrogen gas by means of degassing.

The hyperpolarisation process as well as the injection process take place while the magnetic field inside field cycling magnet 2 is low (such as earth's magnetic field); typically the magnet 2 is switched off during this time. If desired, a spin-locking oscillating magnetic field may be applied by means of coils 8 (typically RF coils) in order to prevent an early conversion of the singlet or pseudo singlet state into observable (and rapidly decaying) magnetization in the substrate molecules.

At the end of the hyperpolarisation and the injection process, the magnet 2 is switched to a higher field (such as 0.5 Tesla) for inducing a conversion of the polarization in the singlet state or pseudo singlet state into observable magnetization and for detection of NMR signals; the switching is done by means of magnet power supply 7 and typically takes less than one second. If a spin-locking oscillating magnetic field was applied before, it is stopped now. Prior to detecting NMR signals from the hyperpolarised substrate molecules or their metabolites, RF and/or gradient pulse sequences can be applied by means of the coils 8 which are controlled by a control device 9, to enhance and/or complete the conversion. Alternatively, gradient pulses can be applied by means of gradient coils 10 which are also controlled by control device 9. The coils 8, the gradient coils 10 and the control device 9 constitute the components of an NMR device which are also used to obtain NMR (MRI or MRS) signals from the hyperpolarised substrate molecules or their metabolites within the patient 6.

If desired, after a first NMR measurement (or measurement phase), the magnet 2 can be switched off again, to prepare a further NMR measurement (or measurement phase) with the already injected, remaining hyperpolarized substrate molecules. The further NMR measurement is preceded by switching the magnet on again.

During the hyperpolarisation process, it may be desirable to provide a magnetic field strength at the position of polarisation device 3 which is lower than the earth's magnetic field. The gradient coils 10 under control of control device 9 can be utilised to generate a magnetic field of the same strength as the earth's magnetic field but of opposing direction such as to generate a magnetic field strength essentially equal to zero.

Figure 2:
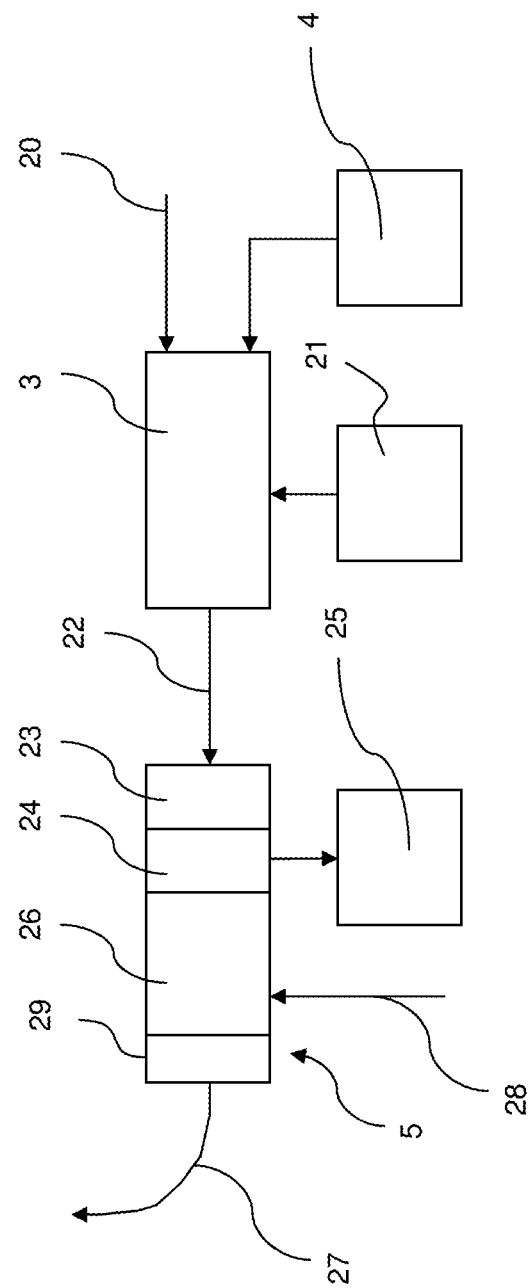
FIG. 2 shows schematically the polarization device and the injection/infusion device of FIG. 1 in more detail.

FIG. 2 illustrates the polarization device 3 and the injection/infusion device 5 in more detail.

A liquid sample containing hyperpolarisable substrate molecules is injected into the polarisation device 3 via a sample injection port 20. The polarisation device 3 contains means (not shown) for bringing the sample into contact with parahydrogen which is supplied to polarisation device 3 from parahydrogen supply device 4 (such as a pressurized $pH_2$ reservoir). The sample may also contain a catalyst for NH-PHIP. Alternatively, the catalyst is introduced into polarising device 3 in solid form. The temperature of the sample containing the hyperpolarisable substrate molecule is controlled by means of temperature control device 21.

The hyperpolarised sample, with substrate molecules in a singlet or pseudo singlet state, is transferred from the polarisation device 3 via transfer conduit 22 e.g. by pneumatic means (not shown) into the injection/infusion device 5. The injection/infusion device 5 contains a filter 23 to remove unwanted components such as the catalyst from the sample. Excess dissolved parahydrogen gas can be removed by means of degassing device 24 which is connected to a vacuum pump 25. If desired (and shown in FIG. 2), the injection/infusion device 5 may also comprise a quality assurance device 29 for monitoring vital parameters, in particular pH and/or temperature of the sample and/or concentration of the substrate molecules in the sample. An injection/infusion pump 26 transfers the biocompatible sample to the patient via injection/infusion conduit 27.

Optionally, after injection of the biocompatible sample into the patient, a solution containing a conversion molecule can be introduced into the injection/infusion pump 26 via an injection port 28 for subsequent injection into the patient. Typically, the solution containing the conversion molecules has been filtered before injection into port 28. The conversion molecule may enhance the conversion of the singlet or pseudo singlet state into observable magnetization within the patient. If desired, the solution containing the conversion molecule may be injected in separate portions, so only part of the substrate molecules contained in the patient are converted at each injection of a portion.

Typical Substrate Molecules and Experimental Data on Polarization Conversion

A substrate for use according to the inventive method should contain at least two magnetically coupled spins that are ideally isochronous, although situations where the difference in Zeeman interaction energy is small compared to the spin-spin interaction energy would also be commensurate with the invention. Examples of such molecules that contain aromatic protons can be found in the substrates pyrazine, pyridine, pyradizine, pyrimidine, tetrazines, and/or their derivatives. Motifs such as these are commonly found in drugs where for example Varenicline and Cadralazine represent examples. Alternatively, such a situation can be replicated within aliphatic $CH_2$, or even $CH_3$ groups or their derivatives. The introduction of $^2H$ labelling will further increase the lifetime. Additional motifs include $^{13}C$—$^{13}C$ and $^{15}N$—$^{15}N$ spin pairs which will be specifically synthesised in molecules such as Varenicline and Cadralazine.

Figure 3:
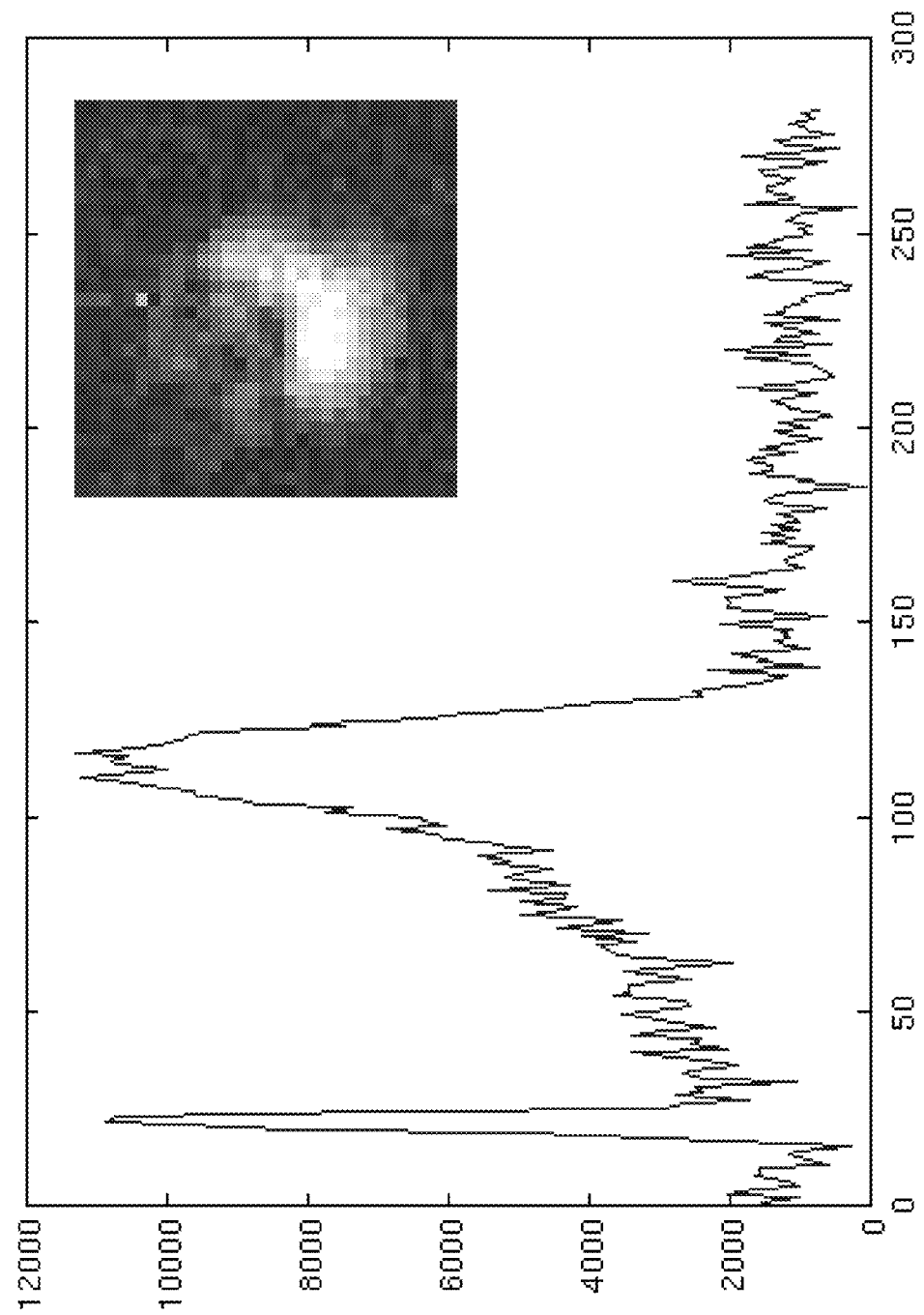
FIG. 3 shows the time course (in seconds) of the MRI signal intensity of pyrazine in an isolated rat heart after hyperpolarization by means of NH-PHIP at low magnetic field; the insert image was acquired 110 seconds after injection of the hyperpolarized pyrazine.

The inventors have found that when pyrazine is examined according to the invention, a pseudo singlet state can be created. This state is effectively invisible to routine MR investigation but can be activated through a suitable interaction. This is illustrated in an experiment, where pyrazine was polarised, according to the inventive method, in low magnetic field, thereby favouring the formation of a pseudo singlet state. Following polarisation, the substrate was injected into an isolated rat heart at high magnetic field. Within the heart, the pyrazine molecules come into contact with substances present in the heart tissue which act as conversion molecules, thereby effecting the conversion of the pseudo singlet state to observable magnetisation. The diagram of FIG. 3 illustrates an MRI signal (top axis, in arbitrary units) as a function of time (right axis, in seconds). Initially, immediately after injection, non-singlet derived observable magnetisation is read out (first maximum in FIG. 3, at about 20 s), while the pseudo-singlet state is probed later, resulting in the second maximum which occurs at a much later time (at about 110 s) than expected based on relaxation characteristics associated with normal $T_1$ values. The already substantially prolonged observation time of the pyrazine signal derived from its pseudo singlet state as observed in this experiment can be further extended according to the invention by injecting the hyperpolarized substrate into the heart at low field and switching to high field at a later time.

CONCLUSION

In summary, the invention introduces an NMR experiment on hyperpolarizable magnetic nuclei of substrate molecules in a living human or animal body, with:
a) the substrate molecules are polarized by non-hydrogenating para-hydrogen induced polarization (=NH-PHIP) into a singlet/pseudo singlet state in low magnetic field;
b) the substrate molecules are injected into the living body, wherein said body or a part thereof is already located inside a magnet at low magnetic field;
c) the magnet is switched on to high magnetic field, and in at least part of the substrate molecules, the singlet state/pseudo singlet state is converted into observable magnetisation;
d) an MRI or MRS measurement is carried out with the living body or the part thereof, collecting data from the substrate molecules.

The NMR experiment is well applicable on hyperpolarized nuclei within a patient, with reduced losses of magnetization due to relaxation processes.

Table of reference signs

1 Field cycling apparatus
2 Field cycling magnet (magnet)
3 Polarisation device

Table of reference signs

| | |
|---|---|
| 4 | Parahydrogen supply device |
| 5 | Injection/infusion device |
| 6 | Living human or animal body (patient) |
| 7 | Magnet power supply |
| 8 | Coils |
| 9 | Control device |
| 10 | Gradient coils |
| 20 | Sample injection port |
| 21 | Temperature control device |
| 22 | Sample transfer conduit |
| 23 | Filter |
| 24 | Degassing device |
| 25 | Vacuum pump |
| 26 | Injection/infusion pump |
| 27 | Injection/infusion conduit |
| 28 | Conversion molecule injection port |
| 29 | Quality assurance device |

NON-PATENT LITERATURE REFERENCES

[1] Ardenkjær-Larsen J H, Fridlund B, Gram A, Hansson G, Hansson L, Lerche M H, Servin R, Thaning M, Golman K., *Proc. Natl. Acad. Sci. USA;* 100, 10158-1016. (2003)

[2] Natterer, J., Bargon, J., *Prog. NMR Spectr.* 31, 293-315 (1997)

[3] Adams, R. W., Aguilar, J. A., Atkinson, K. D., Cowley, M. J., Elliott, P. I. P., Duckett, S. B., Green, G. G. R., Khazal, I. G., Lopez-Serrano, J., Williamson, D. C., *Science,* 323, 1708-1711 (2009)

[4] Franzoni, M. B. et al., J. Am. Chem. Soc. 134 (25), pp. 10393-10396 (2012)

We claim:

1. A method for carrying out an MRI or MRS experiment on hyperpolarizable magnetic nuclei of substrate molecules and/or their metabolites contained in a living human or animal body, the method comprising the steps of:
   a) polarizing the substrate molecules and/or their metabolites using non-hydrogenating para-hydrogen induced polarization (=NH-PHIP) into a singlet state or pseudo singlet state in an environment of a static magnetic field lower than 100 mT or lower than 10 mT;
   b) injecting, following step a), the substrate molecules and/or their metabolites, in the singlet state or in the pseudo singlet state, into the living human or animal body, the human or animal body or a part thereof being disposed within a magnet and in a static magnetic field lower than 100 mT or lower than 10 mT;
   c) switching on, following step b), the magnet to produce a static magnetic field strength inside the magnet higher than 200 mT or higher than 500 mT, wherein switching on the magnet converts at least a part of the substrate molecules and/or their metabolites in the singlet state or pseudo singlet state into observable magnetisation; and
   d) carrying out, following step c), an MRI or MRS measurement with the living human or animal body or the part thereof contained inside the magnet, thereby collecting data from the substrate molecules and/or their metabolites.

2. The method of claim 1, wherein, in step c), the magnet is switched on over a time of 5 s or less, 1 s or less or 0.5 s or less.

3. The method of claim 1, wherein the magnet used in the method is of non-superconducting type.

4. The method of claim 1, wherein, in step c), the singlet state or pseudo singlet state of at least part of the substrate molecules and/or their metabolites is spontaneously converted into observable magnetization.

5. The method of claim 1, wherein a spin-locking oscillating magnetic field is applied during steps a) and b), thereby preventing conversion of the singlet or pseudo singlet state into observable magnetization and the spin-locking oscillating magnetic field is switched off in step c).

6. The method of claim 1, wherein an RF pulse sequence and/or a gradient pulse sequence is applied in step c).

7. The method of claim 1, wherein, in step c), the substrate molecule and/or a metabolite is chemically reacted or brought into contact with a conversion molecule.

8. The method of claim 1, further comprising the steps of:
   e) switching the magnet to a static magnetic field strength inside the magnet which is lower than 100 mT or lower than 10 mT and/or a applying a spin-locking oscillating magnetic field;
   f) switching the magnet to a static magnetic field strength inside the magnet higher than 200 mT or higher than 500 mT and/or switching off the spin-locking oscillating magnetic field, wherein at least a part of remaining substrate molecules and/or their metabolites in the singlet state or pseudo singlet state is converted into observable magnetisation;
   g) carrying out a further MRI or MRS measurement with the living human or animal body or the part thereof contained inside the magnet, thereby collecting data from the substrate molecules and/or their metabolites; and
   h) repeating steps e) through g) at least once.

9. The method of claim 8, wherein, in step c) and optionally one or several steps f), the substrate molecule and/or a metabolite is chemically reacted or brought into contact with a conversion molecule, with an amount of the conversion molecule chosen small enough that only a part or only 50% or less of the substrate molecules and/or their metabolites in the singlet state or pseudo singlet state are affected by conversion into observable magnetization.

10. The method of claim 8, wherein, in step d) and optionally one or several steps g), only part of an observable magnetization is measured, is measured by applying a small flip angle excitation pulse or is measured by applying a flip angle pulse of 45° or smaller.

11. The method of claim 1, wherein, during or after step c), a polarization transfer from $^1H$ to other nuclei, to $^{13}C$, to $^{15}N$ to $^{19}F$ or to $^{31}P$, in the substrate molecules and/or metabolites is effected by means of an RF and/or gradient pulse sequence.

12. The method of claim 1, wherein step a) is performed in an environment with a static magnetic field lower than 1 mT or lower than 100 μT.

13. The method of claim 1, wherein step a) is performed in an environment shielded from an earth's magnetic field, a static magnetic field strength in a shielded environment thereby being below 10 μT.

14. The method of claim 1, wherein, in step b), the static magnetic field inside the magnet is lower than 1 mT or lower than 100 μT.

15. The method of claim 1, wherein the magnet is shielded from an earth's magnetic field and, in step b), the static magnetic field inside the magnet is below 10 μT.

16. The method of claim 1, wherein, the static magnetic field in step a) is chosen small enough such that a Zeeman energy of the hyperpolarizable magnetic nuclei in the substrate molecules and/or their metabolites is lower than or equal to a spin-spin interaction energy thereof.

17. The method of claim 1, wherein, in step a), the static magnetic field is chosen such that a Zeeman energy of the hyperpolarizable magnetic nuclei in the substrate molecule and/or a metabolite is larger than a spin-spin interaction energy thereof, and a polarization process is carried out for a prolonged period of time, which is not less than three times, five times or ten times an average time required to transfer a polarisation of parahydrogen to the hyperpolarizable magnetic nuclei of the substrate molecules and/or their metabolites.

18. The method of claim 1, wherein step a) is done in a polarization device placed inside the magnet or in a polarization device placed inside the magnet at a distance of 2 feet or less or of 1 foot or less from the living human or animal body.

19. The method of claim 1, wherein, in step a), the substrate molecules and/or their metabolites are contained in a solution.

20. The method of claim 19, wherein, following step a), the solution containing the substrate molecules and/or their metabolites polarized in the singlet or pseudo-singlet state is converted into a biocompatible solution.

21. The method of claim 19, wherein, following step a), a catalyst is removed from the solution.

22. The method of claim 19, wherein, after step a), the solution is degassed.

23. The method of claim 1, wherein, in step d), NMR signals altered by interaction with further molecules contained in the living human or animal body are collected from the substrate molecules and/or their metabolites.

24. The method of claim 1, wherein, after step b), time is allowed to pass for the substrate molecules and/or their metabolites to be transported or to be transported via a blood stream of the living human or animal body to a region or organ of interest within the living human or animal body and/or for a metabolic process involving the substrate molecule and/or a metabolite to evolve.

25. The method of claim 1, wherein the MRI or MRS experiment includes position sensitive NMR spectroscopy.

26. The method of claim 1, further comprising the step of diagnosing and/or therapy monitoring the living human or animal body.

* * * * *